(12) United States Patent
McKay (10) Patent No.: US 8,070,782 B2
(45) Date of Patent: Dec. 6, 2011

(54) FACET FUSION IMPLANTS AND METHODS OF USE

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/686,747

(22) Filed: Jan. 13, 2010

(65) Prior Publication Data

US 2010/0114175 A1     May 6, 2010

Related U.S. Application Data (62) Division of application No. 11/410,803, filed on Apr. 25, 2006, now abandoned.

(51) Int. Cl.
*A61B 17/88* (2006.01)

(52) U.S. Cl. .......................... 606/279; 606/247

(58) Field of Classification Search .............. 606/247, 606/246, 248, 249, 279, 17.12–17.16, 280–289, 606/70, 71; 623/17.11
See application file for complete search history.

(56) References Cited

U.S. PATENT DOCUMENTS

| | | | |
|---|---|---|---|
| 5,015,255 A | 5/1991 | Kuslich | |
| 5,062,845 A | 11/1991 | Kuslich et al. | |
| 5,300,073 A | 4/1994 | Ray et al. | |
| 5,324,291 A * | 6/1994 | Ries et al. ...................... 606/71 | |
| 5,417,690 A | 5/1995 | Sennett et al. | |
| 5,445,639 A | 8/1995 | Kuslich et al. | |
| 5,491,882 A | 2/1996 | Walston et al. | |
| 5,507,823 A | 4/1996 | Walston et al. | |
| 5,571,191 A | 11/1996 | Fitz | |
| 5,577,995 A | 11/1996 | Walker et al. | |
| 5,603,713 A | 2/1997 | Aust et al. | |
| 5,741,261 A | 4/1998 | Moskovitz et al. | |
| 5,776,198 A * | 7/1998 | Rabbe et al. ................ 623/17.15 |
| 5,879,396 A | 3/1999 | Walston et al. | |
| 6,015,436 A * | 1/2000 | Schonhoffer .............. 623/17.16 |
| RE36,758 E | 6/2000 | Fitz | |

(Continued)

FOREIGN PATENT DOCUMENTS

DE     20112123    * 10/2001

OTHER PUBLICATIONS

English Translation of DE20112123, McElroy Translation Company, Feb. 2008.*

*Primary Examiner* — Eduardo C Robert
*Assistant Examiner* — Jan Christopher Merene (57) ABSTRACT

An implant is insertable onto a vertebral facet joint includes a body with an inner surface that mates with one or both articular processes of the facet joint. The inner surface may define an interior cavity that accepts at least a portion of an inferior articular process and a superior articular process forming the facet joint. The body may be constructed of a bone growth material that fuses with the articular processes. The implant may help retain bone growth promoting substance that is inserted between or on articulating surfaces of the facet joint. A receiving portion of an exterior surface of one or both articular process may be prepared to stimulate bone growth. The implant may be placed onto the receiving portion to cover an exterior junction between or on the articulating surfaces of the facet joint. The implant may be secured to one or both of the articular processes.

18 Claims, 9 Drawing Sheets

U.S. PATENT DOCUMENTS

| | | | |
|---|---|---|---|
| 6,132,464 A | 10/2000 | Martin | |
| 6,200,322 B1 | 3/2001 | Branch et al. | |
| 6,312,431 B1 | 11/2001 | Asfora | |
| 6,565,605 B2 | 5/2003 | Goble et al. | |
| 6,579,319 B2 | 6/2003 | Goble et al. | |
| 6,610,091 B1 | 8/2003 | Reiley | |
| 6,626,944 B1 | 9/2003 | Taylor | |
| 6,660,007 B2 * | 12/2003 | Khanna | 606/284 |
| 6,811,567 B2 | 11/2004 | Reiley | |
| 7,087,084 B2 | 8/2006 | Reiley | |
| 7,101,398 B2 | 9/2006 | Dooris et al. | |
| 7,147,664 B2 * | 12/2006 | Louis et al. | 623/17.11 |
| 7,169,150 B2 * | 1/2007 | Shipp et al. | 606/287 |
| 7,517,358 B2 | 4/2009 | Petersen | |
| 7,537,611 B2 | 5/2009 | Lee | |
| 7,601,170 B2 | 10/2009 | Winslow et al. | |
| 7,744,630 B2 * | 6/2010 | Lancial | 606/247 |
| 7,892,267 B2 * | 2/2011 | Lancial et al. | 606/304 |
| 2002/0151899 A1 * | 10/2002 | Bailey et al. | 606/69 |
| 2003/0125740 A1 * | 7/2003 | Khanna | 606/61 |
| 2003/0187443 A1 * | 10/2003 | Lauryssen et al. | 606/71 |
| 2004/0087948 A1 * | 5/2004 | Suddaby | 606/61 |
| 2004/0127989 A1 | 7/2004 | Dooris et al. | |
| 2005/0124993 A1 * | 6/2005 | Chappuis | 606/61 |
| 2006/0004367 A1 | 1/2006 | Alamin et al. | |
| 2006/0149374 A1 | 7/2006 | Winslow et al. | |
| 2006/0189989 A1 * | 8/2006 | Bert | 606/69 |
| 2006/0190081 A1 | 8/2006 | Kraus et al. | |
| 2006/0229618 A1 * | 10/2006 | Dube | 606/69 |
| 2007/0055373 A1 * | 3/2007 | Hudgins et al. | 623/17.11 |
| 2007/0083266 A1 | 4/2007 | Lang | |
| 2007/0112428 A1 | 5/2007 | Lancial | 623/17.12 |
| 2009/0036986 A1 * | 2/2009 | Lancial et al. | 623/17.11 |

* cited by examiner

FACET FUSION IMPLANTS AND METHODS OF USE

The present application is a divisional application of U.S. patent application Ser. No. 11/410,803 filed on Apr. 25, 2006, herein incorporated by reference in its entirety.

BACKGROUND

The human spine serves many functions. The vertebral members of the spinal column protect the spinal cord. The spinal column also supports other portions of the human body. Furthermore, moveable facet joints and resilient discs disposed between the vertebral members permit motion between individual vertebral members. Each vertebrae includes an anterior body and a posterior arch. The posterior arch includes two pedicles and two laminae that join together to form the spinous process. A transverse process is laterally positioned at the transition from the pedicles to the laminae. Both the spinous process and transverse process provide for attachment of fibrous tissue, including muscle. Two inferior articular processes extend downward from the junction of the laminae and the transverse process. Further, two superior articular processes extend upward from the junction. The articular processes of adjacent vertebrae form the facet joints. The inferior articular process of one vertebra articulates with the superior articular process of the vertebra below. The facet joints are gliding joints because the articular surfaces glide over each other.

Vertebral implants are often used in the surgical treatment of spinal disorders such as degenerative disc disease, disc herniations, curvature abnormalities, and trauma. Many different types of treatments are used. In some cases, spinal fusion is indicated to inhibit relative motion between vertebral bodies. Spinal fusion often involves the removal of the vertebral disc and insertion of an interbody implant to create a fused junction between a pair of vertebral bodies. Furthermore, the facet joints may be fused to complete the fusion between vertebral pairs. Facet fusion often involves destruction of the facet by decorticating the opposing articulating surfaces and packing bone growth promoting substances such as grafts or synthetic materials into the space between the articular processes. The facet joints are generally small as compared to the intervertebral space. Consequently, limited amounts of bone-growth promoting substances may be inserted into the joint. Some of the bone-growth promoting substances tend to disperse post-operatively resulting in a less robust fusion. Furthermore, the overlying fibrous tissue may further disperse the bone-growth promoting substances as a result of contact, friction, and/or the ingrowth of fibrous mass. These and other factors may result in pseudarthrosis or inadequate fusion.

SUMMARY

Illustrative embodiments disclosed herein are directed to an implant that is insertable onto a vertebral facet joint. The implant includes a body with an inner bone-contact surface that is configured to fuse with the articular processes. The inner surface may define an interior cavity that is configured to accept at least a portion of an inferior articular process and a superior articular process forming the facet joint. The inner surface may include curved and/or planar portions. The body may be constructed of a bone growth material that fuses with the articular processes. The implant body may be constructed from manufactured materials that include bone growth promoting materials and/or bone ingrowth promoting features.

The implant may be used in conjunction with bone growth promoting materials that are packed into the facet joint. The implant may help retain the bone growth promoting substance between the articulating surfaces of the facet joint. The implant may also protect the bone growth promoting substance from adjacent muscle compression and fibrous tissue invasion and may improve bone fusion rate and size of the fusion mass. A receiving portion of an exterior surface of one or both articular process may be prepared to stimulate bone growth. The implant may be placed onto the receiving portion to cover an exterior junction between the articulating surfaces of the facet joint. The implant may be secured to one or both of the articular processes. For example, the implant may be staked, pinned, screwed, or adhered to the exterior of one or both articular processes.

DETAILED DESCRIPTION

Figure 1:
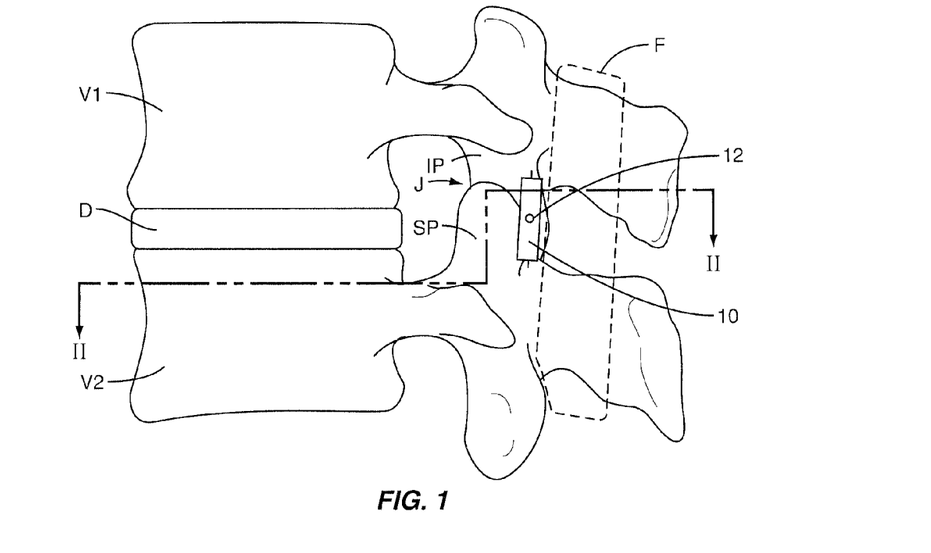
FIG. 1 is a lateral view of a facet implant according to one embodiment shown relative to vertebral bodies.

The various embodiments disclosed herein relate to an implant in which a graft plate or cap is disposed over the exterior of a facet joint to promote fusion of the facet in spinal fusion surgery. FIG. 1 illustrates one embodiment of an implant 10 installed in this manner. Specifically, FIG. 1 shows a lateral view of two vertebrae V1, V2 and an intervertebral disc D disposed therebetween. During fusion surgery, some or all of the disc D is removed and may be replaced with an implant or graft that ultimately fuses to the vertebrae V1, V2. In addition, a surgeon may elect to fuse the facet joints J that are formed between the inferior articular process IP of the superior vertebra V1 and the superior articular process SP of the inferior vertebra V2. To that end, the implant 10 may be attached to the articular processes IP, SP as illustrated and disclosed herein. In one or more embodiments, the implant 10 may be pinned or screwed to the articular processes IP, SP using a fastener 12. The fastener 12 may be implemented using a pin, a nail, a screw, a staple, a wedge, or other feature that secures the implant 10 to the facet joint J until fusion occurs. Other embodiments disclosed herein may be implemented without a fastener 12.

In one or more embodiments, the implant 10 is disposed over the exterior of the facet joint J in a manner that physically separates the facet joint J from fibrous tissue (e.g., muscle and ligaments) that is depicted generally by the dashed lines and the letter F in FIG. 1. Further, the exemplary implant 10 serves as a cap that covers the posterior junction between the inferior articular process IP of the superior vertebra V1 and the superior articular process SP of the inferior vertebra V2. The implant 10 and fastener 12 may be constructed of biocompatible materials, including metals, such as titanium or stainless steel, non-metals, such as PEEK or UHMWPE. The implant 10 and fastener 12 may be constructed of a graft material, which is interpreted herein to include implants constructed from natural or synthetic bone materials including, but not limited to autograft, allograft, xenograft, or calcium phosphate. In embodiments where the implant 10 is constructed from synthetic or manufactured materials, the implant 10 may be coated or textured to improve the likelihood of bony ingrowth into the implant. Similarly, the implant may be impregnated, packed, or filled with bone growth promoting substances such as Bone Morphogenetic Protein (BMP), demineralized bone matrix (DBM), allograft, autograft, xenograft, or other osteoinductive growth factors. For example, the implant 10 may have a porous structure with open portions of the implant 10 packed with the bone growth promoting substance. In certain implementations, the implant 10 may osseointegrate or become part of the fusion mass at the facet joint J to increase the size and stability of the fusion mass. In one embodiment, the fastener 12 may be constructed from a bioabsorbable material that begins to dissolve after the implant 10 has begun to fuse to the facet joint J.

Figure 2:
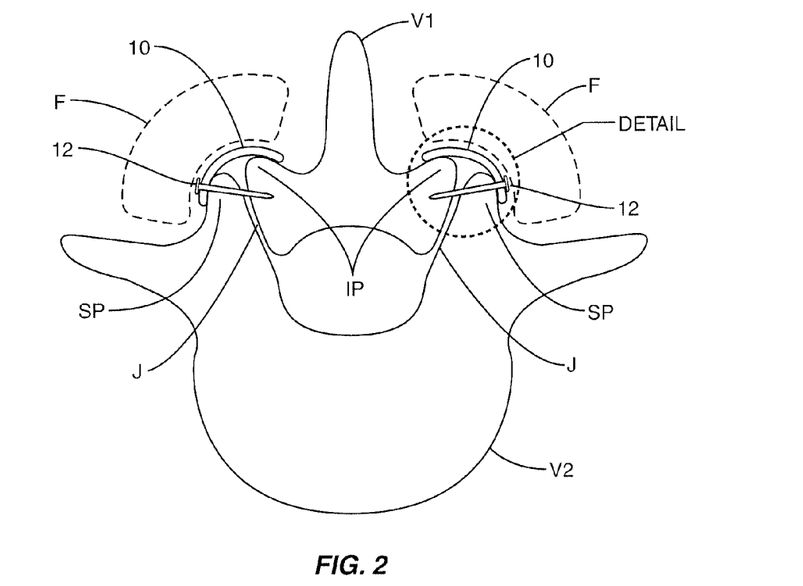
FIG. 2 is a section view according to the section lines in FIG. 1.

The section view shown in FIG. 2 is depicted according to the section line labeled II-II in FIG. 1. The exemplary implant 10 illustrated in FIG. 1 is also presented in FIG. 2. As described above, this embodiment of the implant 10 is disposed so that it covers the posterior side of the facet joint J and forms a barrier between joint J and the fibrous tissue F that covers the facet joint J. In other embodiments, the implant 10 may cover other portions of the facet joint, including lateral or anterior junctions between the inferior articular process IP of the superior vertebra V1 and the superior articular process SP of the inferior vertebra V2. Notably, FIG. 2 includes a "DETAIL" callout that identifies the view illustrated in various other Figures. The detail views provide a magnified representation of the facet joint and various embodiments of the implant.

Figure 3:
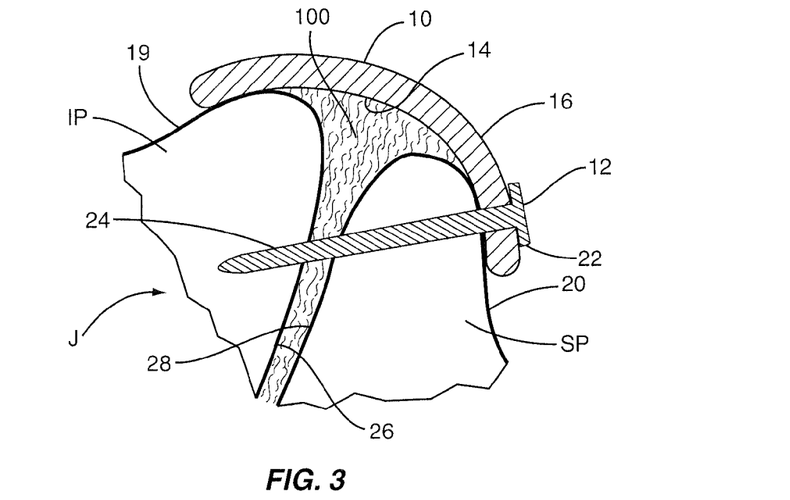
FIG. 3 is a detail view of a facet joint showing one embodiment of a facet implant.

FIG. 3 shows a detail view of the same embodiment of the implant 10 depicted in FIGS. 1 and 2. FIG. 3 further illustrates bone growth promoting material 100 that is packed between the articular processes IP, SP that form the facet joint J. These bone growth promoting materials 100 are often used in an attempt to fuse the facet joint J and stabilize a motion segment of the spine. The fusion process may involve some destruction of the facet, including removing cartilage at the interface surfaces 26, 28, decorticating each interface surface 26, 28, and packing the bone growth promoting material 100 into the joint J in an attempt to promote new bone growth that will ultimately fuse the facet joint J. Some non-limiting examples of bone growth promoting substances that may be inserted into the facet joint J include Bone Morphogenetic Protein (BMP), demineralized bone matrix (DBM), allograft, autograft, xenograft, or other osteoinductive growth factors to facilitate fusion of the facet joint J.

An inner surface 14 of the implant 10 is positioned so that it contacts outer cortical surfaces 19, 20 of the inferior articular process IP and the superior articular process SP, respectively. In one embodiment, the implant 10 is generally curved to match the anatomy of the outer, cortical surfaces 19, 20. As such, the implant 10 may include an elongated, curved shape as illustrated in the perspective view in FIG. 4. Other shapes are possible as the various embodiments described below bear out.

The exemplary implant 10 covers the facet joint J by an amount that helps prevent the bone growth promoting substance 100 from evacuating the facet joint J. Further, the exemplary implant 10 may act as a barrier to prevent the migration of fibroblasts or other ingrowth of fibrous matter F (see FIGS. 1 and 2) that lies over or adjacent the facet joint J. The implant 10 may be secured as described above with a fastener 12 that extends through the implant 10, from the outer surface 16, and engages one or both of the articular processes IP, SP. In one embodiment, the implant 10 includes an aperture 18 through which the fastener 12 may pass. Additional apertures 18 may be included in the implant 10. The fastener 12 includes an enlarged head 22 and elongated body 24. The length of the illustrated body 24 is sufficient to engage both of the articular processes IP, SP. That is, the fastener 12 passes through the implant 10, through the superior articular process SP, across the interface surfaces 26, 28, and into the inferior articular process IP. In the embodiment shown, the aperture 18 is disposed in proximity to the superior articular process SP so that the fastener 12 initially engages the superior articular process SP of the inferior vertebra V2. In one embodiment, the aperture 18 is disposed so that the fastener 12 initially engages an inferior articular process IP of a superior vertebra V1. Certainly, the length of the elongated body 24 may be shortened so that it engages only one of the articular processes IP, SP that form the facet joint J.

The fastener 12 may require a pilot hole for attachment of the implant 10 over the facet joint J. Thus, in one implementation, the implant may be positioned as desired. Then, a pilot hole may be drilled into the articular processes IP and/or SP using the aperture 18 as a guide. Then, if necessary, the implant may be removed and bone growth promoting material 100 inserted into the facet joint J, between the interface surfaces 26, 28, and under the implant 10 as desired. The implant 10 is then secured to the articular processes IP, SP by inserting the fastener 12.

Figure 5:
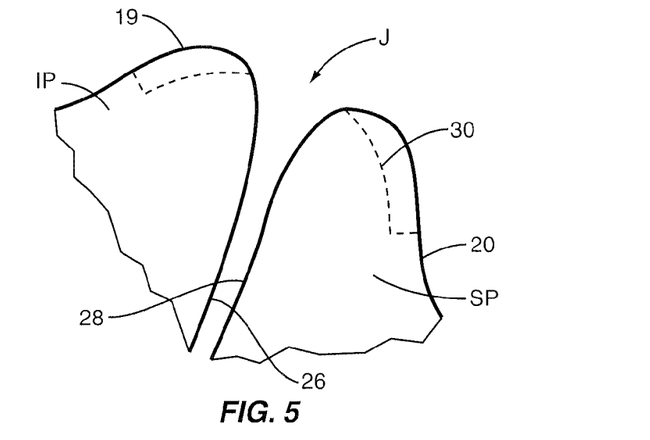
FIG. 5 is a detail view of a facet joint showing the preparation of a receiving area about the exterior of the articular processes according to one embodiment.

The illustrated embodiment of the implant 10 may be attached to the facet joint J without any preparation of the exterior surfaces 19, 20 of the articular processes IP, SP. In another embodiment, the exterior surfaces 19, 20 of the articular processes IP, SP are prepared for the implant 10. As used herein, the term "preparing" is intended to encompass such actions as abrading, ablating, roughening, or scouring such as with an abrading tool (not shown). Alternatively, preparing the exterior surfaces 19, 20 may comprise contouring or decorticating, with bony material removed in preparation for receiving the implant 10. For example, FIG. 5 shows a facet joint J as previously described with a dashed line 30 representing a region of the outer surfaces 19, 20 that are removed using conventionally known techniques. The dashed line 30 represents a receiving portion of the articular processes IP, SP that will receive the implant 10.

Figure 6:
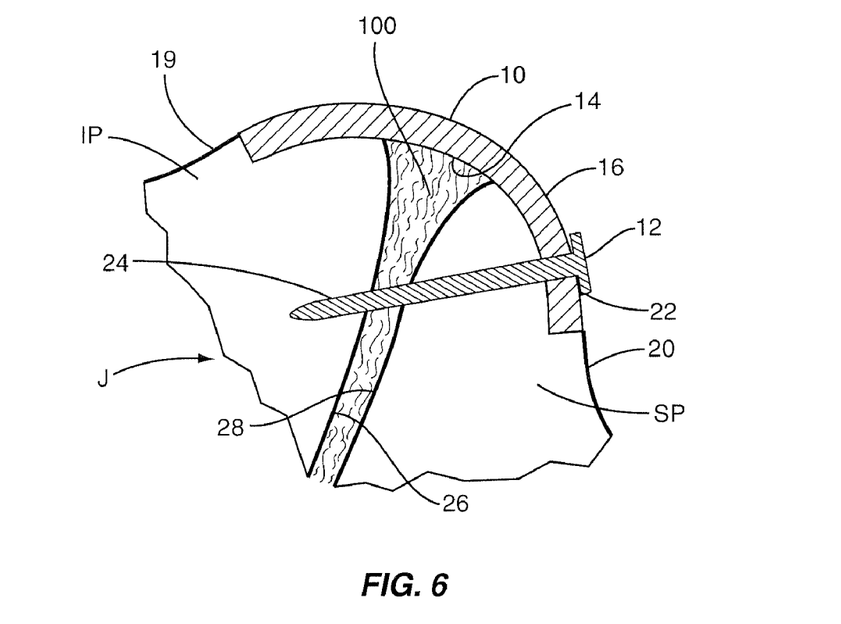
FIG. 6 is a detail view of a facet joint showing one embodiment of a facet implant.
Figure 7:
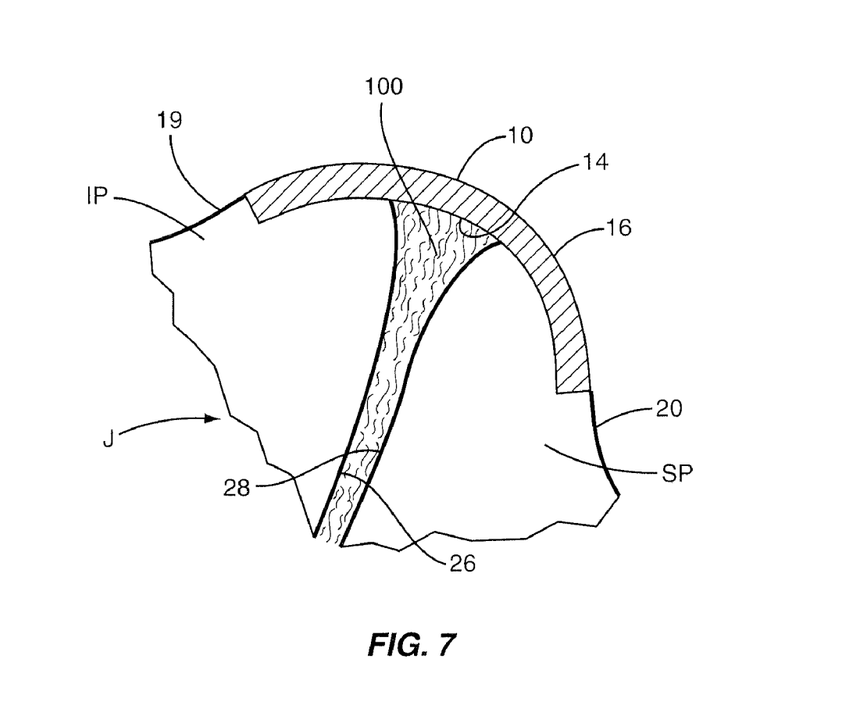
FIG. 7 is a detail view of a facet joint showing one embodiment of a facet implant.

FIG. 6 shows the previously described implant 10 inserted into the receiving portion 30 formerly occupied by the bony material that is removed according to FIG. 5. As above, the implant 10 is retained with a fastener 12. FIG. 7 shows an embodiment in which a similar implant 110 is inserted into a similar receiving portion 30 as in FIGS. 5 and 6. However, in this implementation, a fastener 12 is not used. The overlying fibrous tissue F may retain the implant 110 in the position shown. Further, the implant 110 may be adhered to the articular processes IP, SP with a biocompatible adhesive. Suitable adhesives may include protein derived, aldehyde based adhesive materials, albumin/glutaraldehyde materials, and cyanoacrylate-based materials.

Figure 4:
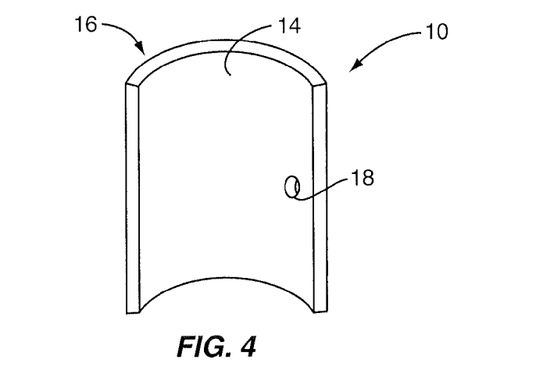
FIG. 4 is a perspective view of a facet implant according to one embodiment.
Figure 8:
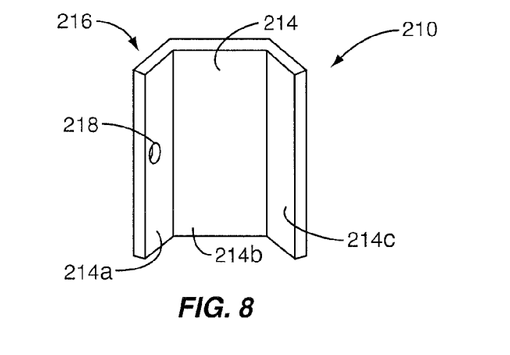
FIG. 8 is a perspective view of a facet implant according to one embodiment.

The previously described implants 10, 110 included a substantially curved construction similar to that shown in FIG. 4. In one embodiment shown in FIG. 8, the implant 210 includes an inner surface 214 and outer surface 216 that are comprised of three substantially planar portions 214a, 214b, 214c oriented at angles relative to one another. In other embodiments, the implant 210 may include a single substantially planar portion or include two planar portions oriented at an angle with respect to each other. In other embodiments, the implant 210 may include four or more substantially planar portions oriented at angles with respect to one another. The angles between the planar portions 14a-c may be configured to substantially match the contour of the exterior surfaces 19, 20 of the facet joint J. The amount of bony material that is removed from the outer surfaces 19, 20 of the facet joint J may be minimized to the extent the implant 210 matches the contour of the exterior surfaces 19, 20. In other implementations, the implant 210 may be attached to a facet joint J where the exterior surfaces 19, 20 are not abraded or decorticated.

Figure 9:
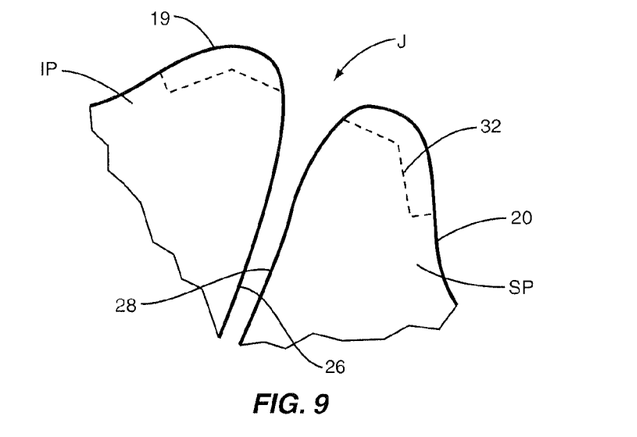
FIG. 9 is a detail view of a facet joint showing the preparation of a receiving area about the exterior of the articular processes according to one embodiment.
Figure 10:
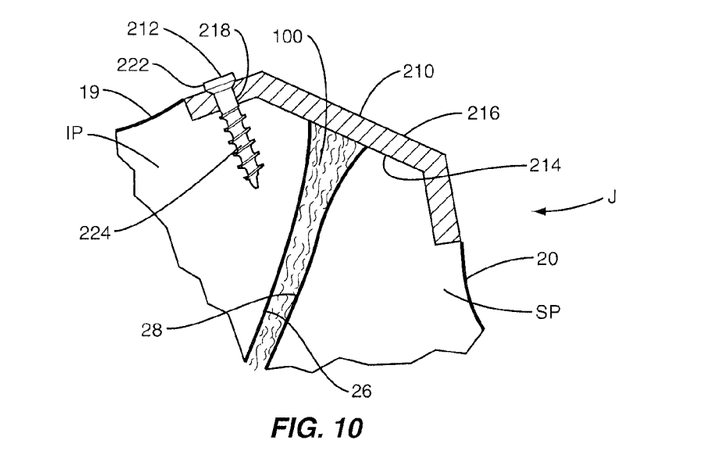
FIG. 10 is a detail view of a facet joint showing one embodiment of a facet implant.

In implementations where the outer cortical surfaces 19, 20 of the facet joint J are decorticated in anticipation of receiving the implant 210, substantially planar faces may be formed in the articular processes IP, SP that substantially match the configuration of the implant 210. For example, FIG. 9 illustrates substantially planar cuts identified by the dashed line 32. FIG. 10 illustrates the exemplary implant 210 inserted against the prepared articular processes IP, SP. In the illustrated embodiment, the implant 210 is secured to the inferior articular process IP with a threaded fastener 212. The threaded fastener 212 includes an enlarged head 222 and a threaded shank 224 that passes through the aperture 218 and into the inferior articular process IP. The threaded fastener 212 may include a drive feature (not shown) disposed in the head 222, such as a hex recess, slotted recess, cross recess, or other driving feature that permits insertion into the facet joint J. In other embodiments, the threaded fastener 212 may engage both articular processes IP, SP. In yet other embodiments, multiple threaded fasteners 212 may be installed to secure the implant 210 to the articular processes IP, SP.

Figure 11:
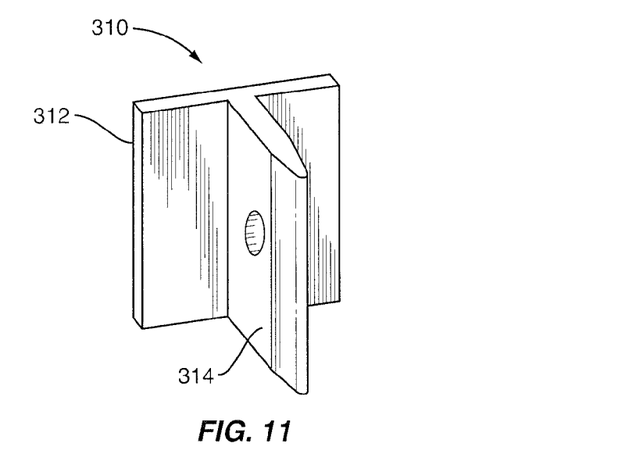
FIG. 11 is a perspective view of a facet implant according to one embodiment.
Figure 12:
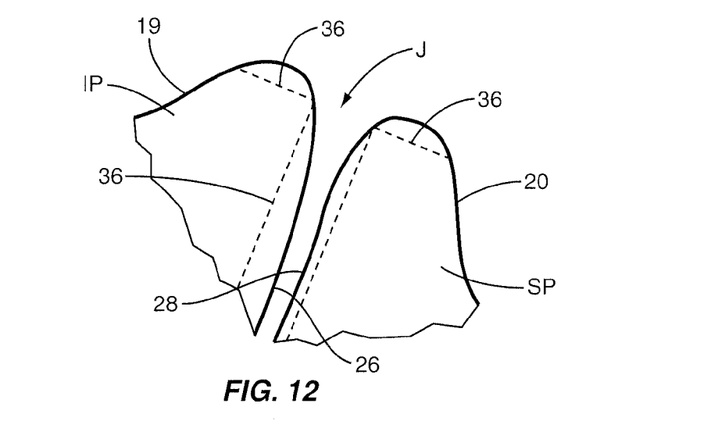
FIG. 12 is a detail view of a facet joint showing the preparation of a receiving area about the exterior of the articular processes according to one embodiment.
Figure 13:
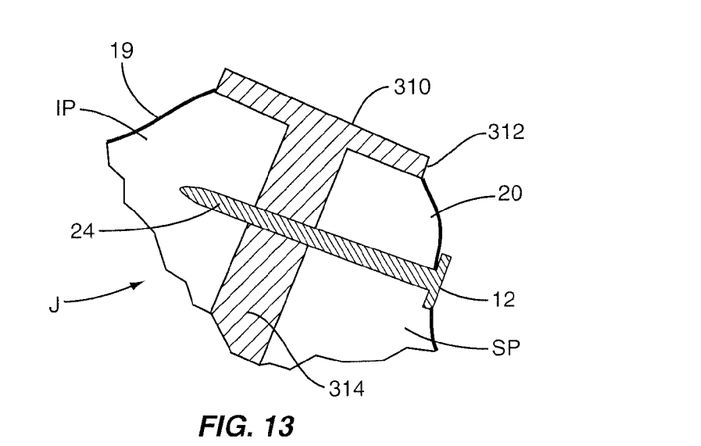
FIG. 13 is a detail view of a facet joint showing one embodiment of a facet implant.

In an embodiment shown in FIG. 11, the implant 310 includes a cover portion 312 and a wedge portion 314 joined together to form a substantially T-shaped implant 310. The cover portion 312 serves a similar purpose to embodiments described above. That is, the cover portion 312 covers the posterior junction between the inferior articular process IP of the superior vertebra V1 and the superior articular process SP of the inferior vertebra V2. Accordingly, the cover portion 312 may include a substantially planar configuration as shown in FIG. 11 or include curved or partially curved configurations similar to previously described embodiments. In contrast with embodiments described above, this implant 310 includes a wedge portion 314 that is positionable within the facet joint J, between the interface surfaces 26, 28 of the articular processes IP, SP. Consequently, in addition to preparing the outer surfaces 19, 20 of the facet joint J to receive the implant 310, the fusion site may benefit from decorticating the interface surfaces 26, 28 as depicted by the dashed lines 36 in FIG. 12. Once the facet joint J is prepared by removing cortical bone as shown in FIG. 12, the implant 310 may be inserted as shown in FIG. 13 and secured with a fastener 12.

Figure 14:
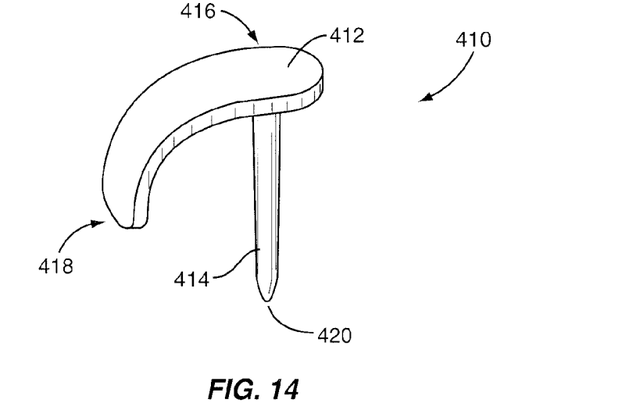
FIG. 14 is a perspective view of a facet implant according to one embodiment.
Figure 15:
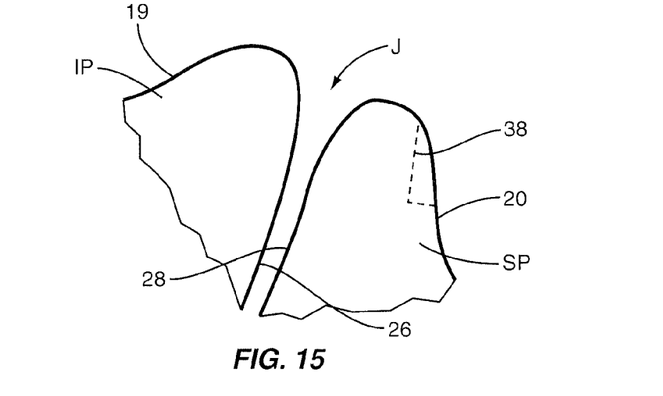
FIG. 15 is a detail view of a facet joint showing the preparation of a receiving area about the exterior of the articular processes according to one embodiment.
Figure 16:
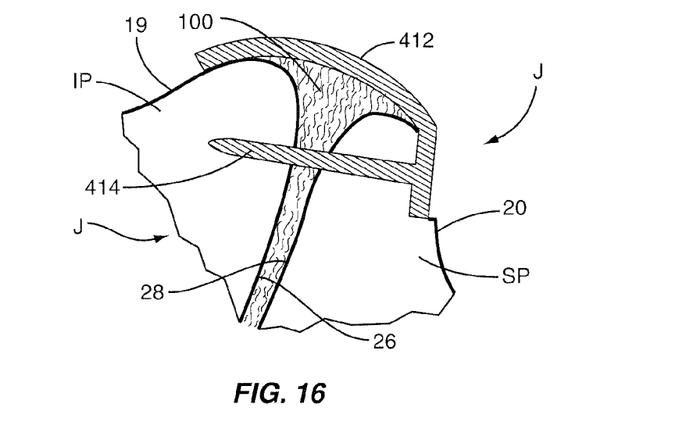
FIG. 16 is a detail view of a facet joint showing one embodiment of a facet implant.

In an embodiment shown in FIGS. 14, 15, and 16, the implant 410 includes an elongated stake 414 and an enlarged head 412. The stake portion 414 is similar to the retainer 12 used in other embodiments in that it includes a pointed insertion tip 420 that can be driven through one or both of the articular processes IP, SP. The head 412, being wider than the stake 414, limits the depth to which the stake 414 is inserted. In one implementation, the outer cortical surfaces 19, 20 of the articular processes IP, SP may be prepared to receive the head 412. In one embodiment shown in FIG. 15, only one of the articular processes SP is decorticated as indicated by dashed line 38 to receive the head 412. In other embodiments, neither or both articular processes IP, SP may be prepared by removing cortical bone.

The enlarged head 412 extends laterally from the stake 414 at a first end 416 and curves along an arcuate path towards a second end 418. The length and curvature of the head 412 may be configured so that the head covers the posterior junction between the inferior articular process IP and the superior articular process SP as shown in FIG. 16. In other embodiments, the head 412 may be formed similar to the head 22 of the retainer 12 shown in other embodiments. That is, the head portion 412 may be configured with a substantially cylindrical or disc shape.

Figure 17:
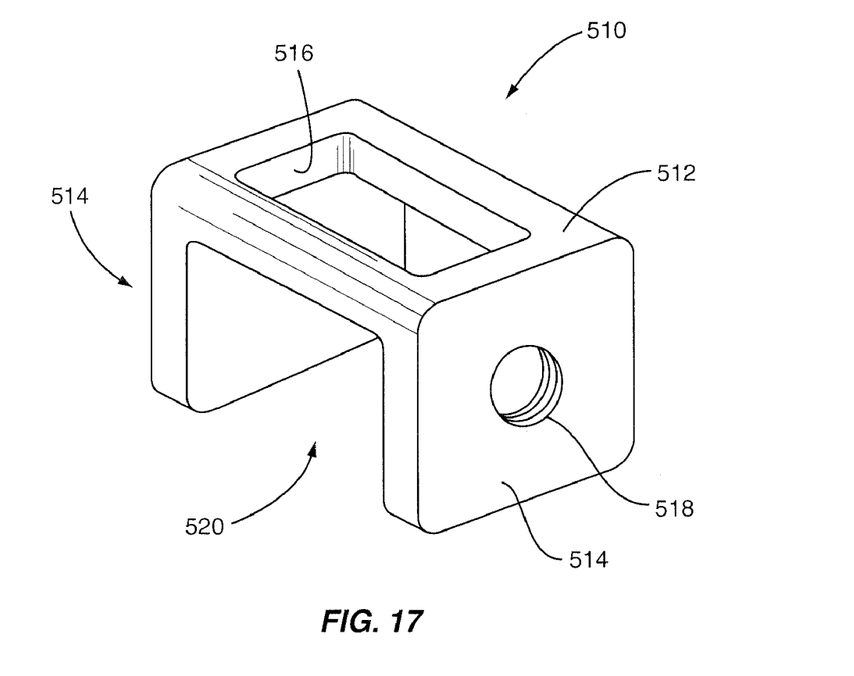
FIG. 17 is a perspective view of a facet implant according to one embodiment.
Figure 18:
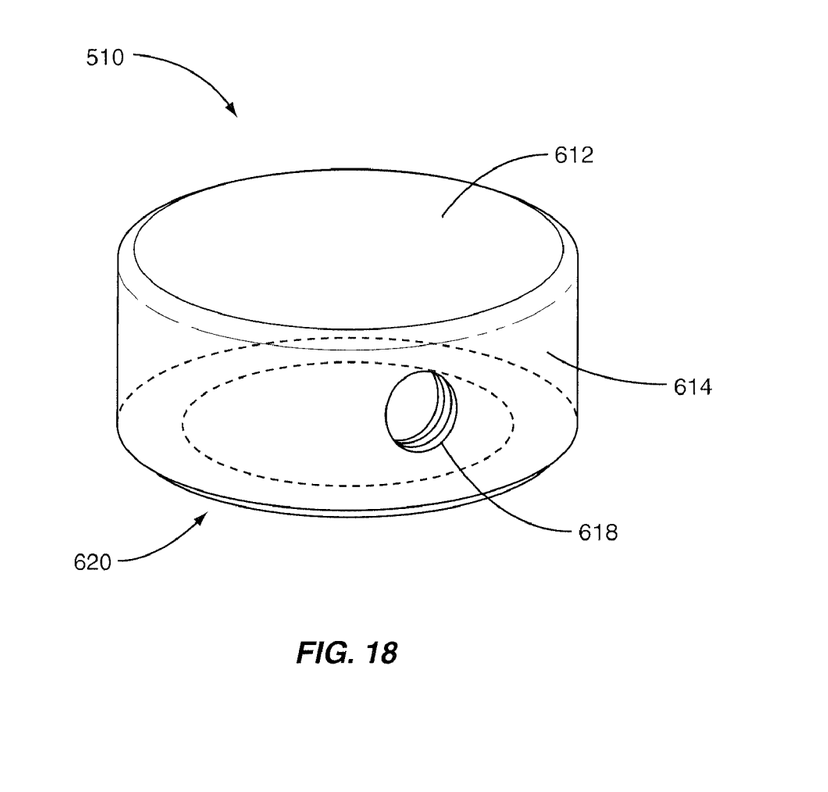
FIG. 18 is a perspective view of a facet implant according to one embodiment.
Figure 19:
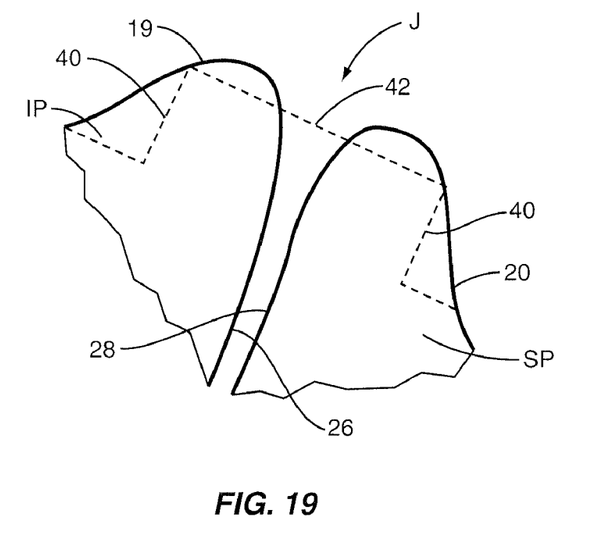
FIG. 19 is a detail view of a facet joint showing the preparation of a receiving area about the exterior of the articular processes according to one embodiment.
Figure 20:
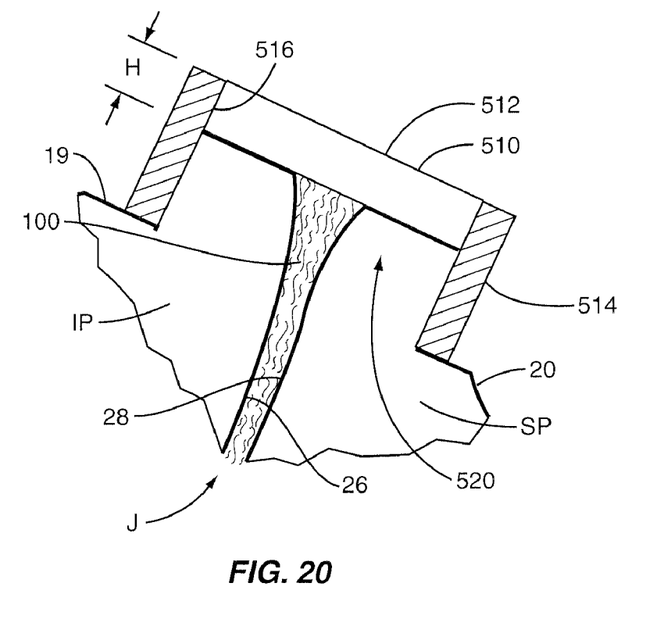
FIG. 20 is a detail view of a facet joint showing one embodiment of a facet implant.
Figure 21:
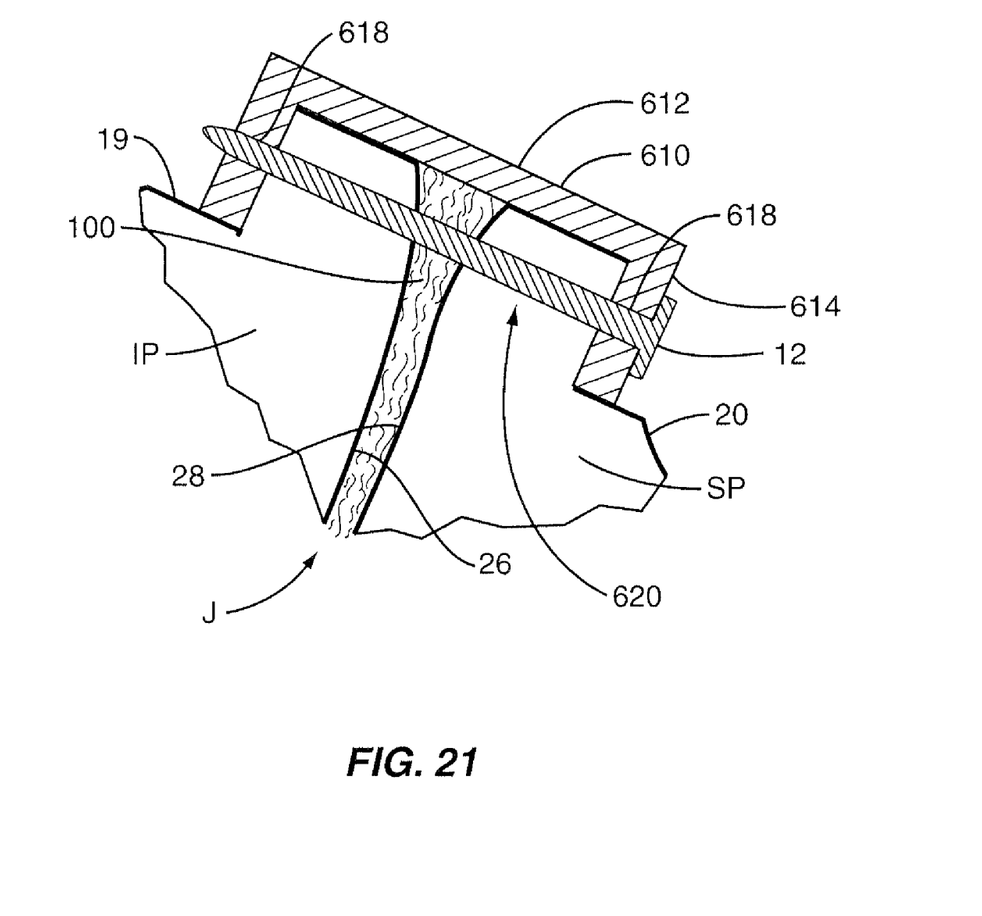
FIG. 21 is a detail view of a facet joint showing one embodiment of a facet implant.

FIGS. 17 and 18 depict implant embodiments 510, 610, that are similar to one another in that lateral sides 514, 614 of the implants 510, 610 extend substantially perpendicular to a substantially planar top surface 512, 612. In each implant 510, 610, the top surface 512, 612 and lateral sides 514, 614 form an open bottom end that leads into an interior cavity 520, 620. In one embodiment, the intersection of the top surface 612 and side surface 614 may be rounded such that the implant 610 includes a substantially continuous outer surface forming a dome shaped structure. The facet joint J may be prepared to receive the implants 510, 610 by removing cortical bone from the exterior surfaces 19, 20 of the articular processes IP, SP as shown in FIG. 19. The dashed line 40 illustrates an exemplary cutting path to accommodate the lateral sides 514, 614 of the implants 510, 610. Dashed line 42 represents a cut that reduces the height of the facet joint J and may be optional depending on the implementation. The cut may traverse a substantially cylindrical path or a square path depending on the shape of the side walls 514, 614 of the implant 510, 610. The prepared facet joint J is inserted into the interior cavity 520, 620 as shown in FIGS. 20 and 21.

FIG. 17 shows that the implant 510 includes an aperture 516 in the top surface 512 through which bone growth promoting material 100 may be inserted. For example, FIG. 20 shows the implant 510 inserted onto the facet joint J and the aperture 516 exposing the interface surfaces 26, 28 to permit packing of the bone growth promoting material 100 between the articular processes IP, SP. Notably, the top surface 512 of the implant 510 is disposed a distance H above the top surface of the articular processes IP, SP, which may advantageously provide a buffer between the packed bone growth promoting material 100 and the overlying fibrous tissue. In FIG. 17, this distance H is relative to an outer surface 19, 20 that is cut according to dashed line 42 in FIG. 19. In other implementations, the height of the articular processes IP, SP may be retained by omitting the cut identified by dashed line 42 in FIG. 19. In either case, the implant 510 can be configured to provide the buffer represented by dimension H.

FIG. 17 also shows that the implant 510 includes two side surfaces 514. Thus, the implant 510 includes a generally inverted U-shaped structure. In other embodiments, the implant 510 may include three or four side surfaces 514 to form a box structure. The implant 510 also includes one or more apertures 518 that are sized to accept one of the aforementioned retainers 12, 212. Alternatively, the implant 510 may be attached to the facet joint J without a retainer 12, 212 as shown in FIG. 20 and using one of the aforementioned adhering techniques.

FIG. 18 also shows that the implant 610 includes one or more apertures 618 that are sized to accept a retainer 12, 212. FIG. 21 illustrates that apertures 618 may be disposed opposite one another so that a retainer 12 can be driven through opposite sides of the side wall 614 and both articular processes IP, SP. Implant 510 may be secured to the facet joint J using a similar configuration.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, while only one of the two facet joints are depicted in the various detailed views provided according to the "DETAIL" callout in FIG. 2, a similar configuration may exist at the facet joint located on the opposite lateral side of the spine. The descriptions disclosed herein are not intended to be limited to facet joints on a single side of the spine. Those skilled in the art will comprehend the symmetry and applicability of the various embodiments disclosed herein. The present embodiments are, therefore, to be considered in all respects as illustrative and not restrictive, and all changes coming within the meaning and equivalency range of the appended claims are intended to be embraced therein.

What is claimed is:

1. A method of inserting an implant onto a facet joint in a patient comprising:
   placing a dome shaped implant with a cavity formed by a cover and continuous lateral sides over an exterior of the facet joint with the continuous lateral sides and the cover of the implant extending over an exterior junction formed by a first articulating surface of an inferior articular process and a second articulating surface of a superior articular process of the facet joint, the lateral sides extend perpendicularly outward from the cover; and
   securing the implant to at least one of the inferior articular process and the superior articular process;
   wherein the implant is constructed of a graft material.

2. The method of claim 1, further comprising causing the implant to osseointegrate to the inferior articular process and the superior articular process.

3. The method of claim 1, further comprising positioning the implant between the facet joint and overlying fibrous tissue located adjacent to the facet joint.

4. The method of claim 1, further comprising positioning an inner surface of the implant having a porous structure against the facet joint.

5. A method of inserting an implant onto a facet joint in a patient comprising:
   preparing a receiving portion of the facet joint by removing a portion of an exterior surface other than an articulating surface of each of an inferior articular process and a superior articular process that form the facet joint;
   placing the implant onto the receiving portion and placing continuous lateral sides of the implant around the facet joint and a cover that extends between the lateral sides over the facet joint and covering a posterior interface formed by the inferior articular process and the superior articular process, the cover being planar and the lateral sides being perpendicular to the cover; and
   attaching the implant to the facet joint;
   wherein the implant is constructed of a graft material.

6. The method of claim 5, wherein placing the implant onto the receiving portion comprises positioning the facet joint within a cavity formed by the lateral sides and the cover.

7. The method of claim 5, further comprising securing the implant to at least one of the inferior articular process and the superior articular process.

8. The method of claim 7, further comprising placing the implant to osseointegrate to at least one of the inferior articular process and the superior articular process.

9. The method of claim 5, wherein preparing the receiving portion comprises contouring the exterior surface of each of the inferior articular process and the superior articular process to match an interior shape of the implant.

10. The method of claim 5, wherein preparing the receiving portion comprises decorticating the exterior surface of each of the inferior articular process and the superior articular process.

11. A method of inserting an implant onto a facet joint in a patient comprising:
    forming a receiving portion by removing portions of an exterior surface other than articulating surfaces of an inferior articular process and a superior articular process that form a facet joint;
    placing a bone growth promoting substance onto the receiving portion and between the articulating surfaces of the facet joint;
    placing a dome shaped cavity of the implant over the receiving portion, the dome shaped cavity formed by a cover and sidewalls that extend perpendicularly outward from the cover; and
    securing the implant to at least one of the inferior articular process and the superior articular process;
    wherein the implant is constructed of a graft material.

12. The method of claim 11, further comprising positioning the implant to osseointegrate to the inferior articular process and the superior articular process.

13. The method of claim 11, further comprising placing the implant over the receiving portion and covering a posterior interface formed by the inferior articular process and the superior articular process.

14. The method of claim 11, further comprising placing the implant onto the receiving portion with the sidewalls of the implant extending around the inferior articular process and the superior articular process and the cover extending over a posterior interface formed by the inferior articular process and the superior articular process.

15. The method of claim 11, wherein securing the implant comprises inserting an elongated fastener into the implant and at least one of the inferior articular process and the superior articular process.

16. The method of claim 11, wherein placing the implant onto the receiving portion comprises placing the implant between the bone growth promoting substance and a fibrous tissue overlying the facet joint.

17. The method of claim 11, wherein placing the implant onto the receiving portion comprises covering an exterior junction formed by the articulating surfaces of the facet joint.

18. The method of claim 11, further comprising positioning an inner surface of the implant having a porous structure against the facet joint.

* * * * *